(12) United States Patent
Keppel (10) Patent No.: US 7,458,972 B2
(45) Date of Patent: *Dec. 2, 2008

(54) ELECTROSURGICAL ELECTRODE HAVING A NON-CONDUCTIVE POROUS CERAMIC COATING

(75) Inventor: David S. Keppel, Longmont, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/728,772

(22) Filed: Mar. 27, 2007

(65) Prior Publication Data

US 2007/0203485 A1 Aug. 30, 2007

Related U.S. Application Data

(63) Continuation of application No. 11/355,725, filed on Feb. 16, 2006, now Pat. No. 7,223,265, which is a continuation of application No. 10/728,211, filed on Dec. 4, 2003, now Pat. No. 7,033,354.

(60) Provisional application No. 60/432,385, filed on Dec. 10, 2002.

(51) Int. Cl.
*A61B 18/14* (2006.01)

(52) U.S. Cl. .............................. 606/41; 606/45; 606/51

(58) Field of Classification Search .................. 606/41, 606/45, 51
See application file for complete search history.

(56) References Cited

U.S. PATENT DOCUMENTS

| 371,664 A | 10/1887 | Brannan et al. |
| 702,472 A | 6/1902 | Pignolet |
| 728,883 A | 5/1903 | Downes |
| 1,586,645 A | 6/1926 | Bierman |
| 1,813,902 A | 7/1931 | Bovie |

(Continued)

FOREIGN PATENT DOCUMENTS

CA 2104423 2/1994

(Continued)

OTHER PUBLICATIONS

Sigel et al. "The Mechanism of Blood Vessel Closure by High Frequency Electrocoagulation" Surgery Gynecology & Obstetrics, Oct. 1965, pp. 823-831.

(Continued)

*Primary Examiner*—Lee S Cohen (57) ABSTRACT

An electrosurgical electrode assembly and method utilizing the same are disclosed capable of controlling or limiting the current per arc in real-time during an electrosurgical procedure. The conductive electrosurgical electrode is configured for being connected to an electrosurgical generator system and has a non-conductive, porous ceramic coating that "pinches" or splits the arc current generated by the electrosurgical generator system into the smaller diameter pores of the coating, effectively keeping the same current and voltage, but creating several smaller diameter arcs from one larger diameter arc. This has the effect of separating the arc current, effectively increasing the current frequency, resulting in a finer cut or other surgical effect. That is, the non-conductive, porous ceramic coating enables a low frequency current to achieve surgical results indicative of a high frequency current, while minimizing or preventing thermal damage to adjacent tissue.

20 Claims, 4 Drawing Sheets

U.S. PATENT DOCUMENTS

| | | |
|---|---|---|
| 2,002,594 A | 5/1935 | Wappler et al. |
| 2,011,169 A | 8/1935 | Wappler |
| 2,031,682 A | 2/1936 | Wappler et al. |
| 2,176,479 A | 10/1939 | Willis |
| 2,279,753 A | 4/1942 | Knopp |
| 2,305,156 A | 12/1942 | Grubel |
| 2,632,661 A | 3/1953 | Cristofv |
| 2,668,538 A | 2/1954 | Baker |
| 2,796,065 A | 6/1957 | Kapp |
| 3,459,187 A | 8/1969 | Pallotta |
| 3,643,663 A | 2/1972 | Sutter |
| 3,651,811 A | 3/1972 | Hildebrandt et al. |
| 3,720,896 A | 3/1973 | Beierlein |
| 3,862,630 A | 1/1975 | Balamuth |
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,233,734 A | 11/1980 | Bies |
| 4,300,564 A | 11/1981 | Furihata |
| D263,020 S | 2/1982 | Rau, III |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,452,246 A | 6/1984 | Bader et al. |
| 4,492,231 A | 1/1985 | Auth |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,827,929 A | 5/1989 | Hodge |
| 4,846,171 A | 7/1989 | Kauphusman et al. |
| 4,887,612 A | 12/1989 | Esser et al. |
| 4,938,761 A | 7/1990 | Ensslin |
| 4,985,030 A | 1/1991 | Melzer et al. |
| 5,007,908 A | 4/1991 | Rydell |
| 5,026,370 A | 6/1991 | Lottick |
| 5,035,695 A | 7/1991 | Weber, Jr. et al. |
| 5,084,057 A | 1/1992 | Green et al. |
| 5,099,840 A | 3/1992 | Goble et al. |
| 5,116,332 A | 5/1992 | Lottick |
| 5,147,357 A | 9/1992 | Rose et al. |
| 5,151,102 A | 9/1992 | Xamiyama et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,290,286 A | 3/1994 | Parins |
| 5,304,203 A | 4/1994 | El-Mallawany et al. |
| 5,308,357 A | 5/1994 | Lichtman |
| 5,314,445 A | 5/1994 | Degwitz et al. |
| 5,318,589 A | 6/1994 | Lichtman |
| 5,324,289 A | 6/1994 | Eggers |
| 5,326,806 A | 7/1994 | Yokoshima et al. |
| 5,330,471 A | 7/1994 | Eggers |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,376,089 A | 12/1994 | Smith |
| 5,383,897 A | 1/1995 | Wholey |
| 5,389,098 A | 2/1995 | Tsuruta et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,411,519 A | 5/1995 | Tovey et al. |
| 5,411,520 A | 5/1995 | Nash et al. |
| 5,413,571 A | 5/1995 | Katsaros et al. |
| 5,415,657 A | 5/1995 | Taymor-Luria |
| 5,422,567 A | 6/1995 | Matsunaga |
| 5,423,810 A | 6/1995 | Goble et al. |
| 5,425,690 A | 6/1995 | Chang |
| 5,425,739 A | 6/1995 | Jessen |
| 5,429,616 A | 7/1995 | Schaffer |
| 5,431,672 A | 7/1995 | Cote et al. |
| 5,431,674 A | 7/1995 | Basile et al. |
| 5,437,292 A | 8/1995 | Kipshidze et al. |
| 5,438,302 A | 8/1995 | Goble |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,451,224 A | 9/1995 | Goble et al. |
| 5,456,684 A | 10/1995 | Schmidt et al. |
| 5,458,598 A | 10/1995 | Feinberg et al. |
| 5,460,629 A | 10/1995 | Shlain et al. |
| 5,462,546 A | 10/1995 | Rydell |
| 5,472,443 A | 12/1995 | Cordis et al. |
| 5,478,351 A | 12/1995 | Meade et al. |
| 5,480,409 A | 1/1996 | Riza |
| 5,484,436 A | 1/1996 | Eggers et al. |
| 5,496,312 A | 3/1996 | Klicek |

| | | | | | |
|---|---|---|---|---|---|
| 5,496,317 A | 3/1996 | Goble et al. | 5,792,177 A | 8/1998 | Kaseda |
| 5,496,347 A | 3/1996 | Hashiguchi et al. | 5,797,927 A | 8/1998 | Yoon |
| 5,499,997 A | 3/1996 | Sharpe et al. | 5,797,938 A | 8/1998 | Paraschac et al. |
| 5,509,922 A | 4/1996 | Aranyi et al. | 5,797,941 A | 8/1998 | Schulze et al. |
| 5,514,134 A | 5/1996 | Rydell et al. | 5,797,958 A | 8/1998 | Yoon |
| 5,527,313 A | 6/1996 | Scott et al. | 5,800,449 A | 9/1998 | Wales |
| 5,531,744 A | 7/1996 | Nardella et al. | 5,807,393 A | 9/1998 | Williamson, IV et al. |
| 5,536,251 A | 7/1996 | Evard et al. | 5,810,808 A | 9/1998 | Eggers |
| 5,540,684 A | 7/1996 | Hassler, Jr. | 5,810,811 A | 9/1998 | Yates et al. |
| 5,540,685 A | 7/1996 | Parins et al. | 5,810,877 A | 9/1998 | Roth et al. |
| 5,540,715 A | 7/1996 | Katsaros et al. | 5,814,043 A | 9/1998 | Shapeton |
| 5,542,945 A | 8/1996 | Fritzsch | 5,817,083 A | 10/1998 | Shemesh et al. |
| 5,558,671 A | 9/1996 | Yates | 5,820,630 A | 10/1998 | Lind |
| 5,558,672 A | 9/1996 | Edwards et al. | 5,827,271 A | 10/1998 | Buysse et al. |
| 5,562,699 A | 10/1996 | Heimberger et al. | 5,827,279 A | 10/1998 | Hughett et al. |
| 5,569,241 A | 10/1996 | Edwards | 5,827,281 A | 10/1998 | Levin |
| 5,569,243 A | 10/1996 | Kortenbach et al. | 5,827,323 A | 10/1998 | Klieman et al. |
| 5,571,100 A | 11/1996 | Goble et al. | 5,827,548 A | 10/1998 | Lavallee et al. |
| 5,573,424 A | 11/1996 | Poppe | 5,833,690 A | 11/1998 | Yates et al. |
| 5,573,534 A | 11/1996 | Stone | 5,843,080 A | 12/1998 | Fleenor et al. |
| 5,573,535 A | 11/1996 | Viklund | 5,849,022 A | 12/1998 | Sakashita et al. |
| 5,575,805 A | 11/1996 | Li | 5,853,412 A | 12/1998 | Mayenberger |
| 5,578,052 A | 11/1996 | Koros et al. | 5,860,976 A | 1/1999 | Billings et al. |
| 5,582,611 A | 12/1996 | Tsukagoshi et al. | 5,876,401 A | 3/1999 | Schulze et al. |
| 5,585,896 A | 12/1996 | Yamazaki et al. | 5,882,567 A | 3/1999 | Cavallaro et al. |
| 5,590,570 A | 1/1997 | LeMaire, III et al. | 5,891,141 A | 4/1999 | Rydell |
| 5,601,601 A | 2/1997 | Tal et al. | 5,891,142 A | 4/1999 | Eggers et al. |
| 5,603,711 A | 2/1997 | Parins et al. | 5,893,863 A | 4/1999 | Yoon |
| 5,603,723 A | 2/1997 | Aranyi et al. | 5,893,875 A | 4/1999 | O'Connor et al. |
| 5,611,798 A | 3/1997 | Eggers | 5,893,877 A | 4/1999 | Gampp, Jr. et al. |
| 5,620,453 A | 4/1997 | Nallakrishnan | 5,902,301 A | 5/1999 | Olig |
| 5,624,452 A | 4/1997 | Yates | 5,906,630 A | 5/1999 | Anderhub et al. |
| 5,626,578 A | 5/1997 | Tihon | 5,908,420 A | 6/1999 | Parins et al. |
| 5,626,609 A | 5/1997 | Zvenyatsky et al. | 5,908,432 A | 6/1999 | Pan |
| 5,630,833 A | 5/1997 | Katsaros et al. | 5,911,719 A | 6/1999 | Eggers |
| 5,637,110 A | 6/1997 | Pennybacker et al. | 5,913,874 A | 6/1999 | Berns et al. |
| 5,638,003 A | 6/1997 | Hall | 5,921,984 A | 7/1999 | Sutcu et al. |
| 5,643,294 A | 7/1997 | Tovey et al. | 5,925,043 A | 7/1999 | Kumar et al. |
| 5,647,869 A | 7/1997 | Goble et al. | 5,935,126 A | 8/1999 | Riza |
| 5,647,871 A | 7/1997 | Levine et al. | 5,944,718 A | 8/1999 | Dafforn et al. |
| 5,649,959 A | 7/1997 | Hannam et al. | 5,951,549 A | 9/1999 | Richardson et al. |
| 5,658,281 A | 8/1997 | Heard | 5,954,720 A | 9/1999 | Wilson et al. |
| 5,662,667 A | 9/1997 | Knodel | 5,957,923 A | 9/1999 | Hahnen et al. |
| 5,665,100 A | 9/1997 | Yoon | 5,960,544 A | 10/1999 | Beyers |
| 5,667,526 A | 9/1997 | Levin | 5,961,514 A | 10/1999 | Long et al. |
| 5,674,220 A | 10/1997 | Fox et al. | 5,964,758 A | 10/1999 | Dresden |
| 5,681,282 A | 10/1997 | Eggers et al. | 5,976,132 A | 11/1999 | Morris |
| 5,688,270 A | 11/1997 | Yates et al. | 5,984,939 A | 11/1999 | Yoon |
| 5,693,051 A | 12/1997 | Schulze et al. | 5,989,277 A | 11/1999 | LeMaire, III et al. |
| 5,695,522 A | 12/1997 | LeMaire, III et al. | 5,997,565 A | 12/1999 | Inoue |
| 5,700,261 A | 12/1997 | Brinkerhoff | 6,004,335 A | 12/1999 | Vaitekunas et al. |
| 5,702,390 A | 12/1997 | Austin et al. | 6,010,516 A | 1/2000 | Hulka |
| 5,707,369 A | 1/1998 | Vaitekunas et al. | 6,024,741 A | 2/2000 | Williamson et al. |
| 5,709,680 A | 1/1998 | Yates et al. | 6,024,744 A | 2/2000 | Kese et al. |
| 5,716,366 A | 2/1998 | Yates | 6,030,384 A | 2/2000 | Nezhat |
| 5,720,744 A | 2/1998 | Eggleston et al. | 6,033,399 A | 3/2000 | Gines |
| 5,722,421 A | 3/1998 | Francese et al. | 6,039,733 A | 3/2000 | Buysse et al. |
| 5,725,536 A | 3/1998 | Oberlin et al. | 6,041,679 A | 3/2000 | Slater et al. |
| 5,727,428 A | 3/1998 | LeMaire, III et al. | 6,050,996 A | 4/2000 | Schmaltz et al. |
| 5,735,848 A | 4/1998 | Yates et al. | 6,053,914 A | 4/2000 | Eggers et al. |
| 5,743,906 A | 4/1998 | Parins et al. | 6,053,933 A | 4/2000 | Balazs et al. |
| 5,755,717 A | 5/1998 | Yates et al. | D424,694 S | 5/2000 | Tetzlaff et al. |
| 5,766,130 A | 6/1998 | Selmonosky | D425,201 S | 5/2000 | Tetzlaff et al. |
| 5,766,166 A | 6/1998 | Hooven | 6,059,782 A | 5/2000 | Novak et al. |
| 5,766,170 A | 6/1998 | Eggers | 6,074,386 A | 6/2000 | Goble et al. |
| 5,769,849 A | 6/1998 | Eggers | RE36,795 E | 7/2000 | Rydell |
| 5,772,655 A | 6/1998 | Bauer et al. | 6,083,223 A | 7/2000 | Baker |
| 5,772,670 A | 6/1998 | Brosa | 6,086,586 A | 7/2000 | Hooven |
| 5,776,128 A | 7/1998 | Eggers | 6,090,107 A | 7/2000 | Borgmeier et al. |
| 5,776,130 A | 7/1998 | Buysse et al. | 6,096,037 A | 8/2000 | Mulier et al. |
| 5,779,701 A | 7/1998 | McBrayer et al. | 6,099,550 A | 8/2000 | Yoon |
| H1745 H | 8/1998 | Paraschac | 6,102,909 A | 8/2000 | Chen et al. |
| 5,792,137 A | 8/1998 | Carr et al. | 6,110,171 A | 8/2000 | Rydell |

| | | |
|---|---|---|
| 6,113,596 A | 9/2000 | Hooven et al. |
| 6,113,598 A | 9/2000 | Baker |
| 6,117,158 A | 9/2000 | Measamer et al. |
| 6,123,701 A | 9/2000 | Nezhat |
| H1904 H | 10/2000 | Yates et al. |
| 6,126,658 A | 10/2000 | Baker |
| 6,152,923 A | 11/2000 | Ryan |
| 6,162,220 A | 12/2000 | Nezhat |
| 6,174,309 B1 | 1/2001 | Wrublewski et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,217,602 B1 | 4/2001 | Redmon |
| 6,221,039 B1 | 4/2001 | Durgin et al. |
| 6,224,593 B1 | 5/2001 | Ryan et al. |
| 6,228,080 B1 | 5/2001 | Gines |
| 6,228,083 B1 | 5/2001 | Lands et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,302,424 B1 | 10/2001 | Gisinger et al. |
| 6,319,451 B1 | 11/2001 | Brune |
| 6,322,561 B1 | 11/2001 | Eggers et al. |
| 6,334,860 B1 | 1/2002 | Dorn |
| 6,334,861 B1 | 1/2002 | Chandler et al. |
| 6,345,532 B1 | 2/2002 | Coudray et al. |
| 6,350,264 B1 | 2/2002 | Hooven |
| 6,352,536 B1 | 3/2002 | Buysse et al. |
| 6,358,249 B1 | 3/2002 | Chen et al. |
| 6,358,268 B1 | 3/2002 | Hunt et al. |
| D457,958 S | 5/2002 | Dycus et al. |
| D457,959 S | 5/2002 | Tetzlaff et al. |
| 6,387,094 B1 | 5/2002 | Eitenmuller |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,130 B1 | 10/2002 | Frazier et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,500,176 B1 | 12/2002 | Truckai et al. |
| 6,511,480 B1 | 1/2003 | Tetzlaff et al. |
| 6,514,252 B2 | 2/2003 | Nezhat et al. |
| 6,527,771 B1 | 3/2003 | Weadock et al. |
| 6,558,385 B1 | 5/2003 | McClurken et al. |
| 6,562,037 B2 | 5/2003 | Paton et al. |
| 6,585,735 B1 | 7/2003 | Frazier et al. |
| 6,602,252 B2 | 8/2003 | Mollenauer |
| 6,616,658 B2 | 9/2003 | Ineson |
| 6,616,661 B2 | 9/2003 | Wellman et al. |
| 6,620,161 B2 | 9/2003 | Schulze et al. |
| 6,626,901 B1 | 9/2003 | Treat et al. |
| 6,641,595 B1 | 11/2003 | Moran et al. |
| 6,652,514 B2 | 11/2003 | Ellman et al. |
| 6,652,521 B2 | 11/2003 | Schulze |
| 6,656,177 B2 | 12/2003 | Truckai et al. |
| 6,660,072 B2 | 12/2003 | Chatterjee |
| 6,669,696 B2 | 12/2003 | Bacher et al. |
| 6,676,660 B2 | 1/2004 | Wampler et al. |
| 6,679,882 B1 | 1/2004 | Kornerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,695,840 B2 | 2/2004 | Schulze |
| 6,702,810 B2 | 3/2004 | McClurken et al. |
| 6,726,068 B2 | 4/2004 | Miller |
| 6,726,686 B2 | 4/2004 | Buysse et al. |
| 6,733,498 B2 | 5/2004 | Paton et al. |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,757,977 B2 | 7/2004 | Dambal et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,775,575 B2 | 8/2004 | Bommannan et al. |
| 6,776,780 B2 | 8/2004 | Mulier et al. |
| 6,790,217 B2 | 9/2004 | Schulze et al. |
| 6,796,981 B2 | 9/2004 | Wham et al. |
| D496,997 S | 10/2004 | Dycus et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,860,880 B2 | 3/2005 | Treat et al. |
| 6,887,240 B1 | 5/2005 | Lands et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| 6,942,662 B2 | 9/2005 | Goble et al. |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,977,495 B2 | 12/2005 | Donofrio |
| 6,979,786 B2 | 12/2005 | Aukland et al. |
| 6,994,707 B2 | 2/2006 | Ellman et al. |
| 6,994,709 B2 | 2/2006 | Iida |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,496 B2 | 5/2006 | Yamauchi |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |
| 7,118,587 B2 | 10/2006 | Dycus et al. |

| | | |
|---|---|---|
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| D533,942 S | 12/2006 | Kerr et al. |
| 7,145,757 B2 | 12/2006 | Shea et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |
| 7,160,299 B2 | 1/2007 | Baily |
| 7,169,146 B2 | 1/2007 | Truckai et al. |
| 7,179,258 B2 | 2/2007 | Buysse et al. |
| 7,195,631 B2 | 3/2007 | Dumbauld |
| D541,418 S | 4/2007 | Schechter et al. |
| 7,207,990 B2 | 4/2007 | Lands et al. |
| D541,938 S | 5/2007 | Kerr et al. |
| 7,223,265 B2 * | 5/2007 | Keppel .................. 606/41 |
| 7,232,440 B2 | 6/2007 | Dumbauld et al. |
| 7,241,288 B2 | 7/2007 | Braun |
| 7,241,296 B2 | 7/2007 | Buysse et al. |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,300,435 B2 | 11/2007 | Wham et al. |
| 7,303,557 B2 | 12/2007 | Wham et al. |
| 7,314,471 B2 | 1/2008 | Holman |
| 7,329,256 B2 | 2/2008 | Johnson et al. |
| 7,329,257 B2 | 2/2008 | Kanehira et al. |
| D564,662 S | 3/2008 | Moses et al. |
| 7,342,754 B2 | 3/2008 | Fitzgerald et al. |
| 7,344,268 B2 | 3/2008 | Jigamian |
| 7,367,976 B2 | 5/2008 | Lawes et al. |
| 2002/0013583 A1 | 1/2002 | Camran et al. |
| 2002/0049442 A1 | 4/2002 | Roberts et al. |
| 2002/0099372 A1 | 7/2002 | Schulze et al. |
| 2002/0107517 A1 | 8/2002 | Witt et al. |
| 2002/0111624 A1 | 8/2002 | Witt et al. |
| 2002/0188294 A1 | 12/2002 | Couture et al. |
| 2003/0014052 A1 | 1/2003 | Buysse et al. |
| 2003/0014053 A1 | 1/2003 | Nguyen et al. |
| 2003/0018331 A1 | 1/2003 | Dycus et al. |
| 2003/0018332 A1 | 1/2003 | Schmaltz et al. |
| 2003/0032956 A1 | 2/2003 | Lands et al. |
| 2003/0069571 A1 | 4/2003 | Treat et al. |
| 2003/0078578 A1 | 4/2003 | Truckai Csaba et al. |
| 2003/0109875 A1 | 6/2003 | Tetzlaff et al. |
| 2003/0114851 A1 | 6/2003 | Truckai et al. |
| 2003/0139741 A1 | 7/2003 | Goble et al. |
| 2003/0139742 A1 | 7/2003 | Wampler et al. |
| 2003/0158549 A1 | 8/2003 | Swanson |
| 2003/0181910 A1 | 9/2003 | Dycus et al. |
| 2003/0216732 A1 | 11/2003 | Truckai et al. |
| 2003/0220637 A1 | 11/2003 | Csaba Truckai et al. |
| 2003/0229344 A1 | 12/2003 | Dycus et al. |
| 2003/0236325 A1 | 12/2003 | Bonora |
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0064151 A1 | 4/2004 | Mollenauer |
| 2004/0078035 A1 | 4/2004 | Kanehira et al. |
| 2004/0082952 A1 | 4/2004 | Dycus et al. |
| 2004/0087943 A1 | 5/2004 | Dycus et al. |
| 2004/0115296 A1 | 6/2004 | Duffin |
| 2004/0116924 A1 | 6/2004 | Dycus et al. |
| 2004/0116979 A1 | 6/2004 | Truckai et al. |
| 2004/0122423 A1 | 6/2004 | Dycus et al. |
| 2004/0143263 A1 | 7/2004 | Schechter et al. |
| 2004/0162557 A1 | 8/2004 | Tetzlaff et al. |
| 2004/0193153 A1 | 9/2004 | Sarter et al. |
| 2004/0230189 A1 | 11/2004 | Keppel |
| 2004/0236326 A1 | 11/2004 | Schulze et al. |
| 2004/0243125 A1 | 12/2004 | Dycus et al. |
| 2004/0249371 A1 | 12/2004 | Dycus et al. |
| 2004/0249374 A1 | 12/2004 | Tetzlaff et al. |
| 2004/0260281 A1 | 12/2004 | Baxter, III et al. |
| 2005/0004564 A1 | 1/2005 | Wham et al. |
| 2005/0021025 A1 | 1/2005 | Buysse et al. |
| 2005/0021027 A1 | 1/2005 | Shields et al. |
| 2005/0033278 A1 | 2/2005 | McClurken et al. |
| 2005/0096645 A1 | 5/2005 | Wellman et al. |
| 2005/0101951 A1 | 5/2005 | Wham et al. |
| 2005/0101952 A1 | 5/2005 | Lands et al. |
| 2005/0113818 A1 | 5/2005 | Sartor et al. |
| 2005/0113819 A1 | 5/2005 | Wham et al. |
| 2005/0113826 A1 | 5/2005 | Johnson et al. |
| 2005/0113828 A1 | 5/2005 | Shields et al. |
| 2005/0149017 A1 | 7/2005 | Dycus |
| 2005/0149151 A1 | 7/2005 | Orszulak et al. |
| 2005/0187547 A1 | 8/2005 | Sugi |
| 2005/0197659 A1 | 9/2005 | Bahney |
| 2005/0203504 A1 | 9/2005 | Wham et al. |
| 2005/0240179 A1 | 10/2005 | Buysse et al. |
| 2006/0052778 A1 | 3/2006 | Chapman et al. |
| 2006/0064085 A1 | 3/2006 | Schechter et al. |
| 2006/0074417 A1 | 4/2006 | Cunningham et al. |
| 2006/0079888 A1 | 4/2006 | Mulier et al. |
| 2006/0079890 A1 | 4/2006 | Guerra |
| 2006/0079891 A1 | 4/2006 | Arts et al. |
| 2006/0116675 A1 | 6/2006 | McClurken et al. |
| 2006/0129146 A1 | 6/2006 | Dycus et al. |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0189980 A1 | 8/2006 | Johnson et al. |
| 2006/0189981 A1 | 8/2006 | Dycus et al. |
| 2006/0190035 A1 | 8/2006 | Hushka et al. |
| 2006/0217709 A1 | 9/2006 | Couture et al. |
| 2006/0224158 A1 | 10/2006 | Odom et al. |
| 2006/0259036 A1 | 11/2006 | Tetzlaff et al. |
| 2006/0264922 A1 | 11/2006 | Sartor et al. |
| 2006/0264931 A1 | 11/2006 | Chapman et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0043352 A1 | 2/2007 | Garrison et al. |
| 2007/0043353 A1 | 2/2007 | Dycus et al. |
| 2007/0060919 A1 | 3/2007 | Isaacson et al. |
| 2007/0062017 A1 | 3/2007 | Dycus et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1 | 5/2007 | Dumbauld et al. |
| 2007/0118111 A1 | 5/2007 | Weinberg |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |
| 2007/0156140 A1 | 7/2007 | Baily |
| 2007/0173811 A1 | 7/2007 | Couture et al. |
| 2007/0173814 A1 | 7/2007 | Hixson et al. |
| 2007/0179499 A1 | 8/2007 | Garrison |
| 2007/0203485 A1 | 8/2007 | Keppel |
| 2007/0213706 A1 | 9/2007 | Dumbauld et al. |
| 2007/0213707 A1 | 9/2007 | Dumbauld et al. |
| 2007/0213708 A1 | 9/2007 | Dumbauld et al. |
| 2007/0213712 A1 | 9/2007 | Buysse et al. |

| | | | | | | |
|---|---|---|---|---|---|---|
| 2007/0255279 | A1 | 11/2007 | Buysse et al. | JP | 5-5106 | 1/1993 |
| 2007/0260235 | A1 | 11/2007 | Podhajsky | JP | 5-40112 | 2/1993 |
| 2007/0260238 | A1 | 11/2007 | Guerra | JP | 06343644 A2 | 12/1994 |
| 2007/0260241 | A1 | 11/2007 | Dalla Betta et al. | JP | 07265328 A2 | 10/1995 |
| 2007/0260242 | A1 | 11/2007 | Dycus et al. | JP | 08056955 A2 | 3/1996 |
| 2007/0265616 | A1 | 11/2007 | Couture et al. | JP | 08252263 A2 | 10/1996 |
| 2008/0004616 | A1 | 1/2008 | Patrick | JP | 09010223 A2 | 1/1997 |
| 2008/0009860 | A1 | 1/2008 | Odom | JP | 11244298 A2 | 9/1999 |
| 2008/0015575 | A1 | 1/2008 | Odom et al. | JP | 2000342599 A2 | 12/2000 |
| 2008/0021450 | A1 | 1/2008 | Couture | JP | 2000350732 A2 | 12/2000 |
| 2008/0033428 | A1 | 2/2008 | Artale et al. | JP | 2001008944 A2 | 1/2001 |
| 2008/0039835 | A1 | 2/2008 | Johnson et al. | JP | 2001029356 A2 | 2/2001 |
| 2008/0045947 | A1 | 2/2008 | Johnson et al. | JP | 2001128990 A2 | 5/2001 |
| 2008/0058802 | A1 | 3/2008 | Couture et al. | SU | 401367 | 11/1974 |
| 2008/0082100 | A1 | 4/2008 | Orton et al. | WO | WO 89/00757 | 1/1989 |

FOREIGN PATENT DOCUMENTS

| | | |
|---|---|---|
| WO | WO 92/04873 | 4/1992 |
| WO | WO 92/06642 | 4/1992 |
| DE | 2415263 | 10/1975 |
| WO | WO 94/08524 A | 4/1994 |
| DE | 2627679 | 1/1977 |
| WO | WO 94/20025 | 9/1994 |
| DE | 8712328 | 3/1988 |
| WO | WO 95/02369 | 1/1995 |
| DE | 4303882 | 8/1994 |
| WO | WO 95/07662 | 3/1995 |
| DE | 29616210 | 1/1997 |
| WO | WO 95/15124 | 6/1995 |
| DE | 19608716 | 4/1997 |
| WO | WO 96/05776 | 2/1996 |
| DE | 19751106 | 5/1998 |
| WO | WO 96/22056 | 7/1996 |
| DE | 19751108 | 5/1999 |
| WO | WO 96/13218 | 9/1996 |
| EP | 0364216 A1 | 4/1990 |
| WO | WO 97/00646 | 1/1997 |
| EP | 518230 A1 | 12/1992 |
| WO | WO 97/00647 | 1/1997 |
| EP | 0541930 B1 | 5/1993 |
| WO | WO 97/10764 | 3/1997 |
| EP | 0572131 | 12/1993 |
| WO | WO 97/24073 | 7/1997 |
| EP | 584787 A1 | 3/1994 |
| WO | WO 97/24993 | 7/1997 |
| EP | 0589453 A2 | 3/1994 |
| WO | WO 98/27880 | 7/1998 |
| EP | 0623316 A1 | 11/1994 |
| WO | WO 99/03407 | 1/1999 |
| EP | 0624348 A2 | 11/1994 |
| WO | WO 99/03408 | 1/1999 |
| EP | 0650701 A1 | 5/1995 |
| WO | WO 99/03409 | 1/1999 |
| EP | 0694290 A3 | 3/1996 |
| WO | WO 99/12488 | 3/1999 |
| EP | 0717966 A1 | 6/1996 |
| WO | WO 99/40857 | 8/1999 |
| EP | 0754437 A3 | 3/1997 |
| WO | WO 99/40861 | 8/1999 |
| EP | 853922 A1 | 7/1998 |
| WO | WO 99/51158 | 10/1999 |
| EP | 0875209 A1 | 11/1998 |
| WO | WO 99/66850 A | 12/1999 |
| EP | 0878169 A1 | 11/1998 |
| WO | WO 00/24330 | 5/2000 |
| EP | 0887046 A3 | 1/1999 |
| WO | WO 00/24331 | 5/2000 |
| EP | 0923907 A1 | 6/1999 |
| WO | WO 00/41638 | 7/2000 |
| EP | 0986990 A1 | 3/2000 |
| WO | WO 00/47124 | 8/2000 |
| EP | 1034747 A1 | 9/2000 |
| WO | WO 00/53112 | 9/2000 |
| EP | 1034748 A1 | 9/2000 |
| WO | WO 01/17448 A | 3/2001 |
| EP | 1025807 A3 | 10/2000 |
| WO | WO 01/54604 | 8/2001 |
| EP | 1034746 A3 | 10/2000 |
| WO | WO 02/07627 | 1/2002 |
| EP | 1050278 A1 | 11/2000 |
| WO | WO 02/067798 A1 | 9/2002 |
| EP | 1053719 A1 | 11/2000 |
| WO | WO 02/080783 | 10/2002 |
| EP | 1053720 A1 | 11/2000 |
| WO | WO 02/080784 | 10/2002 |
| EP | 1055399 A1 | 11/2000 |
| WO | WO 02/080785 | 10/2002 |
| EP | 1055400 A1 | 11/2000 |
| WO | WO 02/080786 | 10/2002 |
| EP | 1080694 A1 | 3/2001 |
| WO | WO 02/080793 | 10/2002 |
| EP | 1082944 A1 | 3/2001 |
| WO | WO 02/080794 | 10/2002 |
| EP | 1159926 A2 | 12/2001 |
| WO | WO 02/080795 | 10/2002 |
| EP | 1301135 A | 4/2003 |
| WO | WO 02/080796 | 10/2002 |
| EP | 1330991 A1 | 7/2003 |
| WO | WO 02/080797 | 10/2002 |
| EP | 1486177 A2 | 6/2004 |
| WO | WO 02/080798 | 10/2002 |
| EP | 1472984 A1 | 11/2004 |
| WO | WO 02/080799 | 10/2002 |
| EP | 1527747 A2 | 5/2005 |
| WO | WO 02/081170 | 10/2002 |
| EP | 1530952 A1 | 5/2005 |
| WO | WO 03/090630 A3 | 11/2003 |
| EP | 1532932 A1 | 5/2005 |
| WO | WO 03/101311 | 12/2003 |
| EP | 1535581 A2 | 6/2005 |
| WO | WO 2004/032776 A1 | 4/2004 |
| EP | 1609430 A1 | 12/2005 |
| WO | WO 2004/032777 | 4/2004 |
| EP | 1632192 A1 | 3/2006 |
| WO | WO 2004/052221 | 6/2004 |
| EP | 1645238 A1 | 4/2006 |
| WO | WO 2004/073488 A2 | 9/2004 |
| EP | 1645240 A2 | 4/2006 |
| WO | WO 2004/073490 | 9/2004 |
| EP | 1707143 A1 | 10/2006 |
| WO | WO 2004/073753 | 9/2004 |
| GB | 2214430 A | 6/1989 |
| WO | WO 2004/082495 | 9/2004 |
| GB | 2213416 | 8/1989 |
| WO | WO 2004/098383 | 11/2004 |
| JP | 501068 | 9/1984 |
| WO | WO 2004/103156 | 12/2004 |
| JP | 502328 | 3/1992 |
| WO | 2005/004734 A1 | 1/2005 |
| | | | WO | WO 2005/004735 | 1/2005 |

WO    WO 2005/110264    11/2005

OTHER PUBLICATIONS

Bergdahl et al. "Studies on Coagulation and the Development of an Automatic Computerized Bipolar Coagulator" J.Neurosurg, vol. 75, Jul. 1991, pp. 148-151.

Kennedy et al. "High-burst-strength, feedback-controlled bipolar vessel sealing" Surgical Endoscopy (1998) 12: 876-878.

Peterson et al. "Comparison of Healing Process Following Ligation with Sutures and Bipolar Vessel Sealing" Surgical Technology International (2001).

Linehan et al. "A Phase I Study of the LigaSure Vessel Sealing System in Hepatic Surgery" Section of HPB Surger, Washington University School of Medicine, St. Louis MO, Presented at AHPBA, Feb. 2001.

Johnson et al. "Evaluation of the LigaSure Vessel Sealing System in Hemorrhoidectomy" American College of Surgeons (ACS) Clinicla Congress Poster (2000).

Sayfan et al. "Sutureless Closed Hemorrhoidectomy: A New Technique" Annals of Surgery vol. 234 No. 1 Jul. 2001 pp. 21-24.

Heniford et al. "Initial Results with an Electrothermal Bipolar Vessel Sealer" Surgical Endoscopy (2000) 15:799-801.

Heniford et al. "Initial Research and Clinical Results with an Electrothermal Bipolar Vessel Sealer" Oct. 1999.

McLellan et al. "Vessel Sealing for Hemostasis During Pelvic Surgery" Int'l Federation of Gynecology and Obstetrics FIGO World Congress 2000, Washington, D.C.

Levy et al. "Use of a New Energy-based Vessel Ligation Device During Vaginal Hysterectomy" Int'l Federation of Gynecology and Obstetrics (FIGO) World Congress 1999.

Crawford et al. "Use of the LigaSure Vessel Sealing System in Urologic Cancer Surger" Grand Rounds in Urology 1999 vol. 1 Issue 4 pp. 10-17.

Rothenberg et al. "Use of the LigaSure Vessel Sealing System in Minimally Invasive Surgery in Children" Int'l Pediatric Endosurgery Group (IPEG) 2000.

Palazzo et al. "Randomized clinical trial of Ligasure versus open haemorrhoidectomy" British Journal of Surgery 2002, 89, 154-157.

"Innovations in Electrosurgery" Sales/Product Literature; Dec. 31, 2000.

LigaSure Vessel Sealing System, the Seal of Confidence in General, Gynecologic, Urologic, and Laparaoscopic Surgery Sales/Product Literature; Jan. 2004.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC 2003.

"Reducing Needlestick Injuries in the Operating Room" Sales/Product Literature 2001.

Chung et al., "Clinical Experience of Sutureless Closed Hemorrhoidectomy with LigaSure" Diseases of the Colon & Rectum vol. 46, No. 1 Jan. 2003.

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Paul G. Horgan, "A Novel Technique for Parenchymal Division During Hepatectomy" The American Journal of Surgery, vol. 181, No. 3, Apr. 2001 pp. 236-237.

W. Scott Helton, "LigaSure Vessel Sealing System: Revolutionary Hemostasis Product for General Surgery" Sales/Product Literature 1999.

Michael Choti, "Abdominoperineal Resection with the LigaSure Vessel Sealing System and LigaSure Atlas 20 cm Open Instrument" Innovations That Work, Jun. 2003.

Craig Johnson, "Use of the LigaSure Vessel Sealing System in Bloodless Hemorrhoidectomy" Innovations That Work, Mar. 2000.

Muller et al., "Extended Left Hemicolectomy Using the LigaSure Vessel Sealing System" Innovations That Work,Sep. 1999.

Herman et al., "Laparoscopic Intestinal Resection With the LigaSure Vessel Sealing System: A Case Report" Innovations That Work,Feb. 2002.

Carus et al., "Initial Experience With The LigaSure Vessel Sealing System in Abdominal Surgery" Innovations That Work,Jun. 2002.

Levy et al. "Randomized Trial of Suture Versus Electrosurgical Bipolar Vessel Sealing in Vaginal Hysterectomy" Obstetrics & Gynecology, vol. 102, No. 1, Jul. 2003.

Levy et al., "Update on Hysterectomy—New Technologies and Techniques" OBG Management, Feb. 2003.

Barbara Levy, "Use of a New Vessel Ligation Device During Vaginal Hysterectomy" FIGO 2000, Washington, D.C.

McLellan et al. "Vessel Sealing For Hemostasis During Gynecologic Surgery" Sales/Product Literature 1999.

Sengupta et al., "Use of a Computer-Controlled Bipolar Diathermy System in Radical Prostatectomies and Other Urological Surgery" ANZ Journal of Surgery (2001) 71.9 pp. 538-540.

Olsson et al. "Radical Cystectomy in Females" Current Surgical Techniques in Urology, vol. 14, Issue 3, 2001.

E. David Crawford "Use of a Novel Vessel Sealing Technology in Management of the Dorsal Veinous Complex" Sales/Product Literature 2000.

Jarrett et al., "Use of the LigaSure Vessel Sealing System for Peri-Hilar Vessels in Laparoscopic Nephrectomy" Sales/Product Literature 2000.

E. David Crawford "Evaluation of a New Vessel Sealing Device in Urologic Cancer Surgery" Sales/Product Literature 2000.

Joseph Ortenberg "LigaSure System Used in Laparoscopic 1st and 2nd Stage Orchiopexy" Innovations That Work, Nov. 2002.

Koyle et al., "Laparoscopic Palomo Varicocele Ligation in Children and Adolescents" Pediatric Endosurgery & Innovative Techniques, vol. 6, No. 1, 2002.

Dulemba et al. "Use of a Bipolar Electrothermal Vessel Sealer in Laparoscopically Assisted Vaginal Hysterectomy" Sales/Product Literature, Jan. 2004.

Johnson et al. "Evaluation of a Bipolar electrothermal Vessel Sealing Device in Hemorrhoidectomy" Sales/Product Literature; Jan. 2004.

Int'l Search Report PCT/US98/18640 dated Dec. 17, 1998.
Int'l Search Report PCT/US98/23950 dated Dec. 29, 1998.
Int'l Search Report PCT/US99/24869 dated Feb. 3, 2000.
Int'l Search Report PCT/US01/11218 dated Aug. 3, 2001.
International Search Report PCT/US01/11224 dated Nov. 13, 2001.
Int'l Search Report PCT/US01/11340 dated Aug. 7, 2001.
Int'l Search Report PCT/US01/11420 dated Oct. 8, 2001.
Int'l Search Report PCT/US02/01890 dated Jul. 17, 2002.
Int'l Search Report PCT/US02/11100 dated Jul. 9, 2002.
Int'l Search Report PCT/US04/03436 dated Oct. 5, 2004.
Int'l Search Report PCT/US04/13273 dated Nov. 22, 2004.
Int'l Search Report PCT/US04/15311 dated Nov. 18, 2004.
Int'l Search Report EP 98944778 dated Oct. 31, 2000.
Int'l Search Report EP 98958575.7 dated Sep. 20, 2002.
Int'l Search Report EP 04027314 dated Mar. 10, 2005.
Int'l Search Report EP 04027479 dated Mar. 8, 2005.
Int'l Search Report EP 04027705 dated Feb 3, 2005.
Int'l Search Report EP 04013772 dated Apr. 1, 2005.
Int'l Search Report EP 05013463.4 dated Sep. 28, 2005.
Int'l Search Report EP 05013895 dated Oct. 14, 2005.
Int'l Search Report EP 05016399 dated Jan. 5, 2006.
Int'l Search Report EP 05017281 dated Nov. 16, 2005.
Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021779.3 dated Jan. 18, 2006.
Int'l Search Report EP 05021197.8 dated Jan. 31, 2006.
Int'l Search Report EP 05021937.7 dated Jan. 13, 2006.
Int'l Search Report—extended- EP 05021937.7 dated Mar. 6, 2006.
Int'l Search Report EP 05023017.6 dated Feb. 16, 2006.
Int'l Search Report EP 05021780.1 dated Feb. 9, 2006.
Int'l Search Report EP 06002279.5 dated Mar. 22, 2006.
Int'l Search Report EP 06005185.1 dated Apr. 18, 2006.
Int'l Search Report EP 06006716 dated Aug. 4, 2006.
Int'l Search Report EP 06008779.8 dated Jun. 13, 2006.
Int'l Search Report EP 1683496 dated Jun. 13, 2006.
Int'l Search Report EP 06014461.5 dated Oct. 20, 2006.
Int'l Search Report EP 06020584.6 dated Jan. 12, 2007.
Int'l Search Report EP 06020583.8 dated Jan. 30, 2007.

Int'l Search Report EP 06020756.0 dated Feb. 5, 2007.
Int'l Search Report EP 06024123.9 dated Feb. 26, 2007.
Int'l Search Report EP 04 752343.6 dated Jul. 20, 2007.
Int'l Search Report EP 06 024122.1 dated Mar. 19, 2007.
Int'l Search Report EP 07 001480.8 dated Apr. 12, 2007.
Int'l Search Report EP 07 001488.1 dated May 29, 2007.
Int'l Search Report Extended- EP 07 009029.5 dated Jul. 12, 2007.
Int'l Search Report EP 07 009321.6 dated Aug. 17, 2007.
Int'l Search Report EP 06 020574.7 dated Sep. 21, 2007.
Int'l Search Report EP 07 010672.9 dated Oct. 1, 2007.
Int'l Search Report EP 07 013779.9 dated Oct. 18, 2007.
Int'l Search Report EP 07 009026.1 dated Sep. 12, 2007.
Int'l Search Report EP 07 015601.3 dated Dec. 6, 2007.
Int'l Search Report EP 07 015191.5 dated Dec. 19, 2007.
Int'l Search Report EP 07 020283.3 dated Jan. 16, 2008.

* cited by examiner

ELECTROSURGICAL ELECTRODE HAVING A NON-CONDUCTIVE POROUS CERAMIC COATING

This application is a continuation of U.S. application Ser. No. 11/355,725 filed on Feb. 16, 2006 by David S. Keppel entitled "ELECTROSURGICAL ELECTRODE HAVING A NON-CONDUCTIVE POROUS CERAMIC COATING," now U.S. Pat. No. 7,223,265, which is a continuation of U.S. application Ser. No. 10/728,211 filed on Dec. 4, 2003 by David S. Keppel entitled "ELECTROSURGICAL ELECTRODE HAVING A NON-CONDUCTIVE POROUS CERAMIC COATING," now U.S. Pat. No. 7,033,354, which claims priority from U.S. Provisional Application No. 60/432,385 filed on Dec. 10, 2002 by David S. Keppel entitled "ELECTROSURGICAL ELECTRODE HAVING A NON-CONDUCTIVE POROUS CERAMIC COATING," the entire contents of which are hereby incorporated by reference herein.

BACKGROUND

1. Technical Field

The present disclosure is directed to electrosurgery and, in particular, to an electrosurgical electrode having a non-conductive porous ceramic coating for controlling the amount of current per arc.

2. Description of the Related At

Tissue heating is proportional to the square of the amount of current being generated through the tissue and tissue vaporization is, in turn, generally proportional to current. Vaporization of tissue is proportional to the amount of energy in an arc. This energy, in combination with the Cathode Fall Voltage, derives the power for vaporization. Thermal spread is dependent on the amount of heat generated within the tissue and is dependent on tissue resistivity and the arc energy squared. As can be appreciated, by not controlling the thermal spread the depth of ablation is difficult to predict and control.

Therefore, during electrosurgery, an increase or decrease in the amount of current provides a different tissue effect. This phenomenon is due to a variable referred to as the crest factor (CF). The crest factor can be calculated using the formula: $CF = V_{PEAK}/V_{RMS}$, where $V_{PEAK}$ is the positive peak of the waveform and $V_{RMS}$ is the RMS value of the waveform. The crest factor can also be calculated using the formula: $CF = [(1-D)/D]^{1/2}$, where D is the duty cycle of the waveform and is defined as $D = T_1/(T_1+T_2)$.

Based on the above formulas, it is evident that when operating an electrosurgical generator system in either the "cut", "blend" or "coagulate" mode, the range of the crest factor varies from one mode to another. For example, the "cutting" mode typically entails generating an uninterrupted sinusoidal waveform in the frequency range of 100 kHz to 4 MHz with a crest factor in the range of 1.4 to 2.0. The "blend" mode typically entails generating an uninterrupted cut waveform with a duty cycle in the range of 25% to 75% and a crest factor in the range of 2.0 to 5.0. The "coagulate" mode typically entails generating an uninterrupted waveform with a duty cycle of approximately 10% or less and a crest factor in the range of 5.0 to 12.0. For the purposes herein, "coagulation" is defined as a process of desiccating tissue wherein the tissue cells are ruptured and dried. "Vessel sealing" is defined as the process of liquefying the collagen in the tissue so that it reforms into a fused mass with significantly-reduced demarcation between the opposing tissue structures (opposing walls of the lumen). Coagulation of small vessels is usually sufficient to permanently close them. Larger vessels need to be sealed to assure permanent closure.

An increase in the crest factor results in more current per arc at a given power setting. Further, since tissue heating is proportional to the amount of current through the tissue squared and tissue vaporization is proportional to the amount of current being generated through the tissue, a doubling of current per arc results in four times as much tissue heating and twice the amount of tissue vaporization when an electrode connected to the electrosurgical generator system contacts the tissue. Known electrodes cannot control or limit the current per arc to achieve a particular surgical effect, e.g., a fine cut. Accordingly, such electrodes do not have the ability to manipulate or control the proportion of tissue vaporization to tissue heating, in order to achieve more controllable and desirable surgical effects.

Therefore, it is an aspect of the present disclosure to provide an electrosurgical electrode capable of controlling or limiting the current per arc for controlling the both tissue heating and tissue vaporization.

SUMMARY

An electrosurgical electrode and electrosurgical generator system capable of controlling or limiting the current per arc in real-time during an electrosurgical procedure is disclosed. The conductive electrosurgical electrode is configured for being connected to an electrosurgical generator system and has a non-conductive, porous ceramic coating that "pinches" or splits the arc current generated by the electrosurgical generator system into a small diameter channel, effectively keeping the same current and voltage, but creating several small arcs from one large arc.

This has the effect of separating the arc current, effectively increasing the current frequency, resulting in a finer cut or other surgical effect. That is, the non-conductive, porous ceramic coating enables the application of a low frequency current to achieve surgical results indicative of a high frequency current, while minimizing or preventing thermal damage to adjacent tissue.

The number of small arcs created from one large arc is inversely proportional to the diameter of the pores in the ceramic coating. Preferably, the diameter of each pore is less than the diameter of the arc. Hence, when electrosurgical current is applied to the electrosurgical electrode, the arc current is split between the pores in the electrode, thereby, controlling or limiting the arc current through each pore. This effect which controls or limits the arc current through each pore is referred to as MicroHollow Cathode Discharge (MCD or MHCD).

The diameter of each pore can vary from the diameter of other pores to produce different surgical effects when operating the electrosurgical generator system in one of several modes, such as cut, blend and coagulation modes. In either embodiment, MCD enables the surgeon to control the proportion of tissue vaporization to tissue heating, in order to achieve more controllable and desirable surgical effects.

The number of pores per square centimeter controls the arc area. As the number of pores per square centimeter increases, the arc area decreases, and vice versa. A large arc area is desired when operating the electrosurgical generator system in the coagulation mode and a small arc area is desired when operating in the cut mode. The thickness of the non-conductive, porous ceramic coating controls the system resistance and voltage needed to establish the arc. The thicker the coating the greater the system resistance and voltage needed to establish the arc, and vice versa.

Alternative embodiments provide for the non-conductive, porous ceramic coating to be applied to roller-ball type electrodes for improving the arc distribution across the tissue, and hence, the efficiency of the electrode, as compared to roller-ball type electrodes not coated with the non-conductive, porous ceramic material. Other embodiments and features include modifying the geometry of the electrode before applying the non-conductive, porous ceramic coating on the electrode, so as to control where the arc is split and/or cutting/coagulating occurs, i.e., along edge of the electrode, along length of the electrode, across width of the electrode, etc.

Further, the electrode can be coated accordingly to provide an electrode having at least a portion thereof configured for cutting tissue, at least a portion thereof configured for coagulating tissue, etc. Further still, the pore diameter, the pore length, and/or pore pattern can be varied to produce different effect to control cutting and coagulating tissue.

According to one embodiment of the present disclosure an electrode assembly for controlling the electrosurgical arc current from an electrosurgical generator is disclosed. The electrode assembly includes an electrode having a conductive surface adapted to connect to a source of electrosurgical energy, said electrode having a width and a length. The electrode assembly also includes a non-conductive, porous ceramic material substantially coating said conductive electrode. The non-conductive, porous ceramic material has a predetermined thickness and includes a plurality of pores dispersed therein having a diameter and a depth. The non-conductive, porous ceramic material varies in thickness across the length and width of the electrode. Furthermore, the diameter and the depth of the pores of the non-conductive, porous ceramic material vary across the length and width of the electrode. Upon actuation of the electrosurgical generator, electrosurgical energy from the electrosurgical generator creates an initial arc current across the conductive surface of the electrode. The initial arc current has a diameter greater than the diameter of the pore such that the initial arc current is forced to split into a plurality of subsequent arc currents having a diameter smaller than the diameter of the initial arc current in order to conduct electrosurgical energy through the pores of the non-conductive, porous ceramic material.

According to another embodiment of the present disclosure a method for controlling the amount of electrosurgical energy to tissue is disclosed. The method includes the step of providing an electrode having a conductive surface adapted to connect to a source of electrosurgical energy, said electrode having a a predetermined width and a length. The method also includes the step of coating the electrode with a non-conductive, porous ceramic material having a thickness and a plurality of pores dispersed therein each having a diameter and a depth. The non-conductive, porous ceramic material varies in thickness across at least one of the length and width of the electrode. Furthermore, the diameter and the depth of said pores of said non-conductive, porous ceramic material vary across at least one of a length and a width of the electrode. The method further includes the step of activating the electrosurgical energy source to create an initial arc current across the conductive surface of the electrode. The initial arc has a diameter greater than the diameter of said pores such that the initial arc current is forced to split into a plurality of subsequent arc currents having a smaller diameter than the diameter of the initial arc current in order to conduct electrosurgical energy through the pores of the non-conductive, porous ceramic coating.

According to a further embodiment of the present disclosure an electrode assembly for controlling the electrosurgical arc current from an electrosurgical generator is disclosed. The electrode assembly includes an electrode having a conductive surface adapted to connect to a source of electrosurgical energy. The electrode has a modified geometry adapted for controlling splitting of the electrosurgical arc. The electrode assembly further includes a non-conductive, porous ceramic material substantially coating said conductive electrode, said non-conductive, porous ceramic material has a predetermined thickness and includes a plurality of pores dispersed therein having a diameter and a depth. The diameter of said pores of said non-conductive, porous ceramic material varies across the modified geometry. Upon actuation of the electrosurgical generator, electrosurgical energy from the electrosurgical generator creates an initial arc current across the conductive surface of the electrode. The initial arc current has a diameter greater than the diameter of the pore such that the initial arc current is forced to split into a plurality of subsequent arc currents having a diameter smaller than the diameter of the initial arc current in order to conduct electrosurgical energy through the pores of the non-conductive, porous ceramic material.

Further features of the above embodiments will become more readily apparent to those skilled in the art from the following detailed description of the apparatus taken in conjunction with the drawings.

BRIEF DESCRIPTION OF THE DRAWINGS

Various embodiments will be described herein below with reference to the drawings wherein.

DETAILED DESCRIPTION

Figure 1:
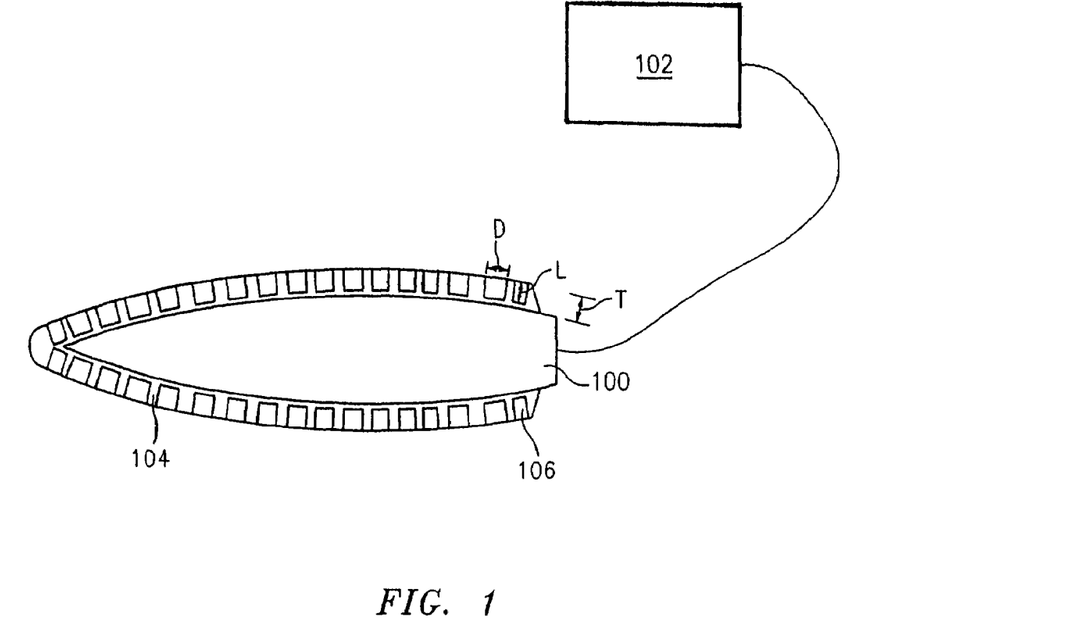
FIG. 1 is an enlarged, cross-sectional view of a portion of a conductive electrode coated with a non-conductive, porous ceramic coating in accordance with the present disclosure.

Reference should be made to the drawings where like reference numerals refer to similar elements. Referring to FIG. 1, there is shown an enlarged, cross-sectional view of one embodiment of a conductive electrode according to the present disclosure. The electrode is designated generally by reference numeral 100 and it is connected to an electrosurgical generator system 102. The electrode 100 is coated with a non-conductive, porous ceramic coating 104 which "pinches" or splits the arc current generated by the electrosurgical generator system 102 into a small diameter channel, effectively keeping the same current and voltage, but creating several small arcs from one large arc.

This has the effect of separating the arc current, effectively increasing the current effect to the tissue, resulting in a finer cut or other surgical effect. That is, the non-conductive, porous ceramic coating 104 enables a low frequency current to achieve surgical results indicative of a high frequency current, while minimizing or preventing thermal damage to adjacent tissue.

The coating 104 includes a plurality of pores 106 having a uniform diameter "D" in the range of 10 μm to 1000 μm and a uniform length "L" (100 to 500 micrometers). The number of small arcs created from one large arc is inversely proportional to the diameter "D" of the pores 106 in the ceramic coating 104. Preferably, the diameter "D" of each pore 106 is less than the diameter of the arc. Hence, when electrosurgical current is applied to the electrosurgical electrode 100, the arc current is split between the pores 106 in the electrode 100, thereby, controlling or limiting the arc current through each pore 106. This effect which controls or limits the arc current through each pore 106 is referred to as "MicroHollow Cathode Discharge" (MCD or MHCD).

Figure 2:
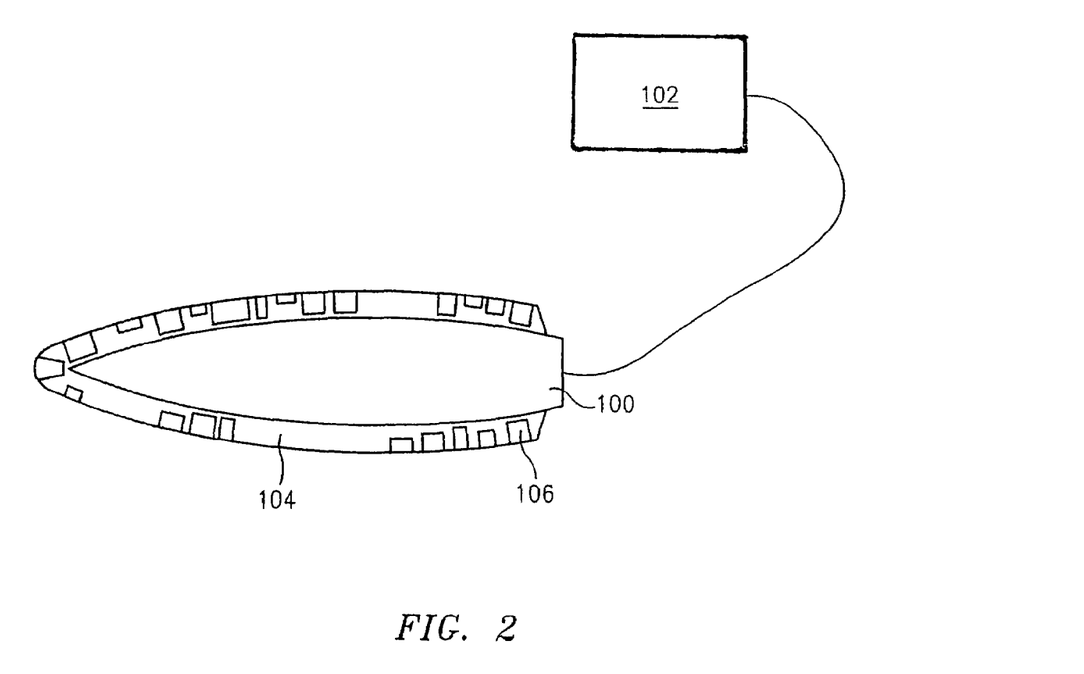
FIG. 2 is an enlarged, cross-sectional view of a conductive electrode coated with a non-conductive, porous ceramic coating having varying pore diameters, varying pore lengths, and varying number of pores per square centimeter in accordance with the present disclosure.

As shown by FIG. 2, it is envisioned that the diameter "D" and the length "L" of the plurality of pores 106 can vary in size to produce different surgical effects when operating the electrosurgical generator system 102 in one of several modes, such as cut, blend and coagulation modes. In either embodiment, MCD enables the surgeon to control the proportion of tissue vaporization to tissue heating, in order to achieve more controllable and desirable surgical effects.

Additionally, as shown by FIG. 2, the number of pores per square centimeter (or the pattern of the pores 106) can be uniform (as shown by FIG. 1) or vary along the length of the electrode 100. The number of pores per square centimeter controls the arc area. As the number of pores per square centimeter increases, the arc area decreases, and vice versa. A large arc area is desired when operating the electrosurgical generator system 102 in the coagulation mode and a small arc area is desired when operating in the cut mode.

The thickness of the non-conductive, porous ceramic coating 104 controls the system resistance and voltage needed to establish the arc. The thicker the coating 104 the greater the system resistance and voltage needed to establish the arc, and vice versa. With continued reference to FIG. 1, the coating 104 has a thickness "T" which is predetermined during fabrication of the electrode 100 for effectively operating the electrode 100 in one of several modes, such as cut, coagulate and blend, by using the electrosurgical generator system 102. A small thickness for the coating 104 in the range of 10 μm to 500 μm is preferred for operating the electrode 100 in the "cut" mode; a medium thickness in the range of 250 μm to 1 mm is preferred for operating the electrode 100 in the "blend" mode; and a large thickness in the range of 500 μm to 2 mm is preferred for operating the electrode 100 in the "coagulate" mode.

Figure 3:
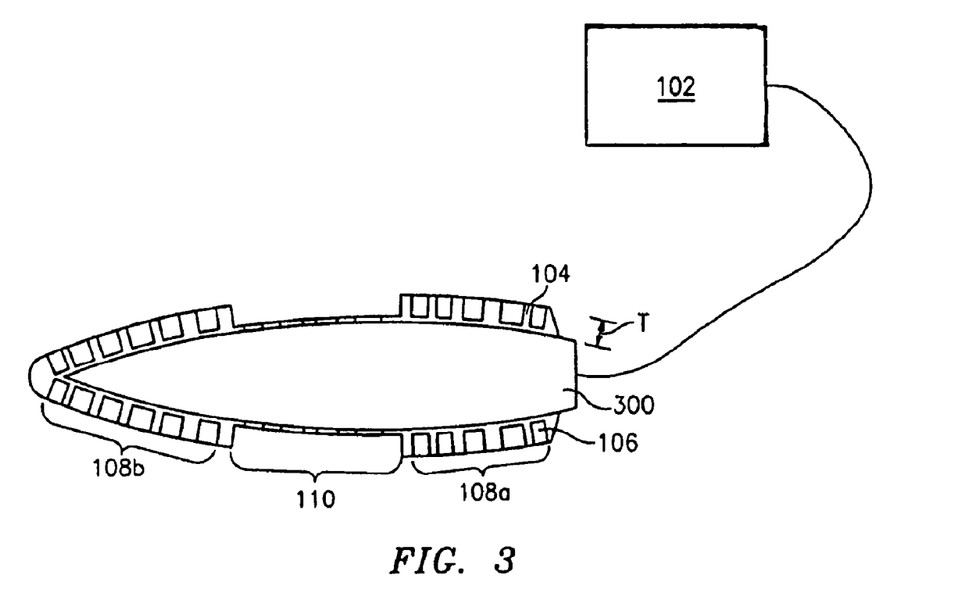
FIG. 3 is an enlarged, cross-sectional view of a conductive electrode coated with a non-conductive, porous ceramic coating with various thicknesses in accordance with the present disclosure.

As shown by FIG. 3, the thickness "T" of the coating 104 can vary at one portion 108 of the electrode 300 with another portion 110 of the electrode 300, in order to be able to effectively operate the electrode 300 in more than one mode by using the electrosurgical generator system 102. The electrode 300 shown by FIG. 3 has two portions 108a, 108b for effectively operating the electrode 300 in the coagulate mode, and one portion 110 for effectively operating the electrode 300 in the cut mode.

It is envisioned that the two opposing jaw members may be created with coating 104 in this manner to simultaneously effect tissue sealing between two opposing 108a portions and 108b portions of each jaw member and effect tissue cutting between two opposing 110 portions. More particularly, the thicker coating areas 108a and 108b on each jaw member will tend to coagulate tissue held there between while the thin coating area 110 will tend to cut tissue held therebetween. As can be appreciated, it is envisioned that a single energy activation may yield a dual tissue effect which greatly simplifies sealing and dividing tissue.

Figure 4:
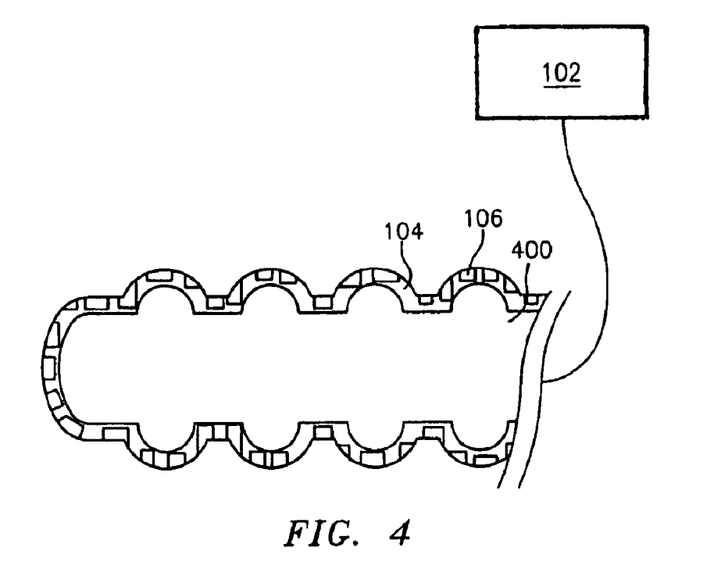
FIG. 4 is an enlarged, cross-sectional view of a roller-ball type, conductive electrode coated with a non-conductive, porous ceramic coating in accordance with the present disclosure.

With reference to FIG. 4, there is shown an enlarged, cross-sectional view of a roller-ball type electrode 400 coated with the non-conductive, porous ceramic coating 104 in accordance with the present disclosure. The coating 104 for this type of electrode improves the arc distribution across the tissue, and hence, the efficiency of the electrode 400, as compared to roller-ball type electrodes not coated with the non-conductive, porous ceramic material.

Figure 5:
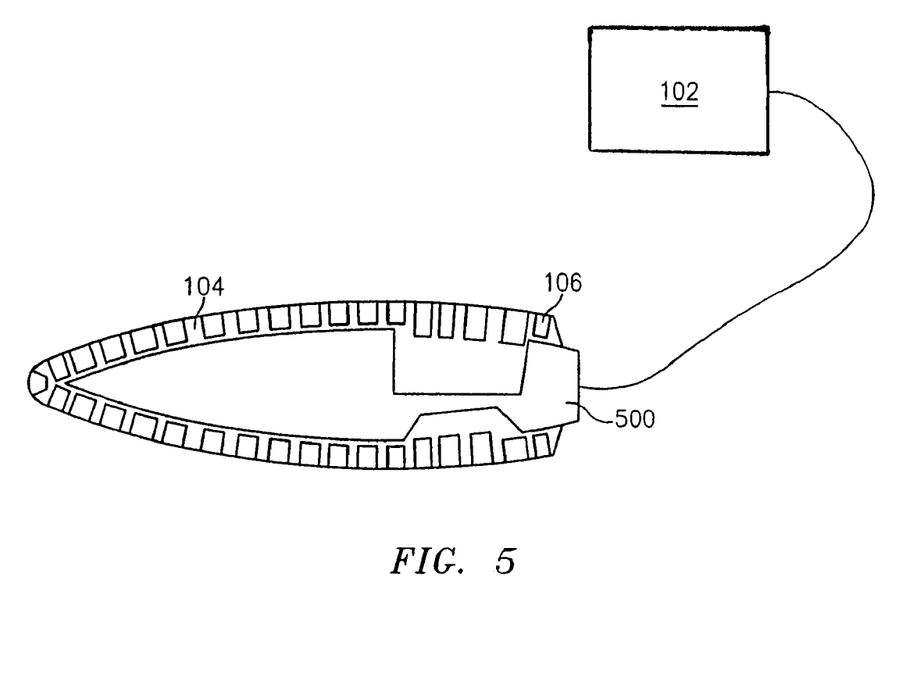
FIG. 5 is an enlarged, cross-sectional view of a conductive electrode having a modified geometry and coated with a non-conductive, porous ceramic coating in accordance with the present disclosure.
Figure 6:
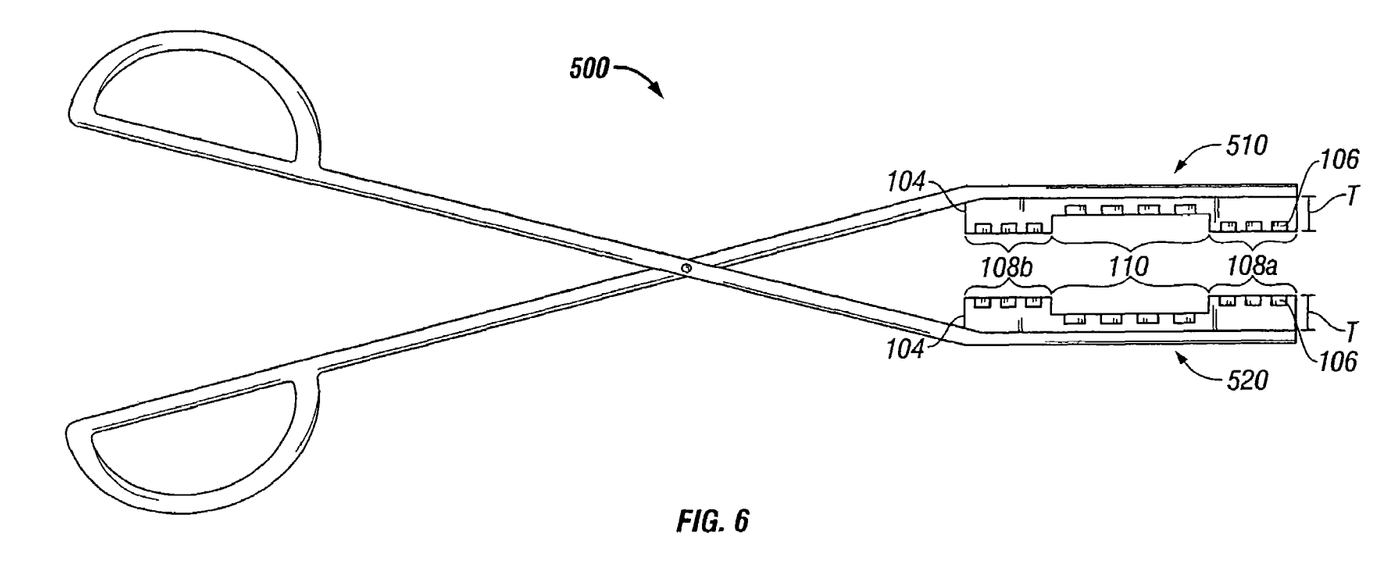
FIG. 6 is an enlarged, cross sectional view of a forceps having two opposing jaw members coated with a non-conductive, porous ceramic coating in according with the present disclosure.

With reference to FIG. 5, there is shown an enlarged, cross-sectional view of an electrode 500 having a modified geometry and coated with the non-conductive, porous ceramic coating 104 in accordance with the present disclosure. The geometrical configuration of the electrode 500 enables control of where the arc is split and/or cutting/coagulating occurs, e.g., along edge of the electrode 500, along the length of electrode 500, across the width of electrode 500, etc. Various diameters, lengths, and patterns (number of pores per square centimeter) for the pores 106 are contemplated besides uniform diameter, length and uniform distribution. Also, a varying or uniform thickness for the coating 104 is contemplated.

The method of the present disclosure includes the steps of providing an electrode having a conductive surface connected to a source of electrosurgical energy, and coating the electrode with a non-conductive, porous ceramic material having a thickness and a plurality of pores dispersed therein each having a diameter. The method further includes the step of activating the electrosurgical energy source to create an initial arc current across the conductive surface of the electrode. The initial arc has a diameter greater than the diameter of the pores such that the initial arc current is forced to split into a plurality of subsequent arc currents having a smaller elevator than the diameter of the initial arc current in order to conduct electrosurgical energy through the pores of the non-conductive, porous ceramic coating.

From the foregoing and with reference to the various figure drawings, those skilled in the art will appreciate that certain modifications can also be made to the present disclosure without departing from the scope of the same. For example, it is envisioned that the pore diameter of the coating 104 may be varied during the manufacturing process according to the type of instrument being used. For example, one size pore diameter may be used for electrosurgical blades for coagulating or cutting tissue which another pore diameter may be used for electrosurgical forceps which utilized a combination of closing force, gap distance between jaw members and electrosurgical energy, to seal tissue. Moreover, it is envisioned that the number of pores per inch may be modified during the manufacturing process to control the arc area and adverse collateral effect to surrounding tissue. It is also contemplated that the thickness of the coating may be modified during manufacturing to establish a preferred resistance and voltage for creating the arc.

Although this disclosure has been described with respect to preferred embodiments, it will be readily apparent to those having ordinary skill in the art to which it appertains that changes and modifications may be made thereto without departing from the spirit or scope of the disclosure.

What is claimed is:

1. An electrode assembly for controlling the electrosurgical arc current from an electrosurgical generator, the electrode assembly comprising:
   an electrode having a conductive surface adapted to connect to a source of electrosurgical energy, said electrode including a width and a length; and
   a non-conductive, porous ceramic material substantially coating said conductive electrode, said non-conductive, porous ceramic material having a thickness and including a plurality of pores dispersed therein having a diameter and a depth, said non-conductive, porous ceramic material varying in thickness across at least one of the length and width of the electrode;
   wherein upon activation of the electrosurgical energy source, electrosurgical energy creates an initial arc current across the conductive surface of the electrode.

2. An electrode assembly according to claim 1, wherein the diameter and depth of said pores of said non-conductive, porous ceramic material vary across at least one of a length and a width of the electrode.

3. An electrode assembly according to claim 1, wherein the initial arc current has a diameter greater than the diameter of the pore such that the initial arc current is forced to split into a plurality of subsequent arc currents having a diameter smaller than the diameter of the initial arc current in order to conduct electrosurgical energy through the pores of the non-conductive, porous ceramic material.

4. An electrode assembly according to claim 1, wherein the number of pores per inch varies across at least one of a length and a width of the electrode.

5. An electrode assembly according to claim 1, wherein the diameter of said pores of said non-conductive, porous ceramic coating is within a range of about 10 to about 1000 micrometers.

6. An electrode assembly according to claim 1, wherein the depth of said pores of said non-conductive, porous ceramic coating is within a range of about 100 to about 500 micrometers.

7. An electrode assembly according to claim 1, wherein the non-conductive, porous ceramic material is dispersed on a pair of opposing jaw members of a forceps.

8. An electrode assembly according to claim 7, wherein the thickness of the non-conductive, ceramic material varies across a length of each of the opposing jaw members.

9. An electrode assembly according to claim 8, wherein the non-conductive, ceramic material on each of the jaw members includes a first thickness dispersed near a distal and a proximal end of each jaw member and a second thickness dispersed between the proximal and distal ends of each jaw member, said first thickness being dimensioned to effectively seal tissues disposed between the opposing jaw members upon electrosurgical activation and said second thickness being dimensioned to effectively cut tissue dispersed between the opposing jaw members upon electrosurgical activation.

10. An electrode assembly according to claim 1, wherein the electrode is at least one of a roller ball electrode and a blade electrode.

11. A method for controlling the amount of electrosurgical energy to tissue comprising the steps of:
    providing an electrode having a conductive surface adapted to connect to a source of electrosurgical energy, said electrode including a width and a length;
    coating said electrode with a non-conductive, porous ceramic material having a thickness and a plurality of pores dispersed therein, said non-conductive, porous ceramic material varying in thickness across at least one of the length and width of the electrode; and
    activating the electrosurgical energy source to create an initial arc current across the conductive surface of the electrode.

12. An electrode assembly for controlling the electrosurgical arc current from an electrosurgical generator, the electrode assembly comprising:
    an electrode having a conductive surface adapted to connect to a source of electrosurgical energy, said electrode having a modified geometry adapted to control the splitting of an arc of electrosurgical energy; and
    a non-conductive, porous ceramic material substantially coating said conductive electrode, said non-conductive, porous ceramic material having a thickness and including a plurality of pores dispersed therein, said non-conductive, porous ceramic material varying in thickness across the modified geometry of said conductive electrode;
    wherein upon activation of the electrosurgical energy source, the electrosurgical energy creates an initial arc current across the conductive surface of the electrode.

13. An electrode assembly according to claim 12, wherein each of the plurality of pores includes a diameter and a depth, the diameter and depth of said pores of said non-conductive, porous ceramic material varying across the modified geometry of said conductive electrode.

14. An electrode assembly according to claim 12, wherein each of the plurality of pores includes a diameter and a depth and wherein the initial arc current has a diameter greater than the diameter of the pore such that the initial arc current is forced to split into a plurality of subsequent arc currents having a diameter smaller than the diameter of the initial arc current in order to conduct electrosurgical energy through the pores of the non-conductive, porous ceramic material.

15. An electrode assembly according to claim 12, wherein the number of pores per inch varies across at least one of a length and a width of the electrode.

16. An electrode assembly according to claim 12, wherein each of the plurality of pores includes a diameter and a depth and wherein the diameter of said pores of said non-conductive, porous ceramic coating is within a range of about 10 to about 1000 micrometers.

17. An electrode assembly according to claim 12, wherein each of the plurality of pores includes a diameter and a depth and wherein the depth of said pores of said non-conductive, porous ceramic coating is within a range of about 100 to about 500 micrometers.

18. An electrode assembly according to claim 12, wherein the non-conductive, porous ceramic material is dispersed on a pair of opposing jaw members of a forceps.

19. An electrode assembly according to claim 18, wherein the thickness of the non-conductive, ceramic material varies across the modified geometry of each of the opposing jaw members.

20. An electrode assembly according to claim 19, wherein the non-conductive, ceramic material on each of the jaw members includes a first thickness dispersed near a distal and a proximal end of each jaw member and a second thickness dispersed between the proximal and distal ends of each jaw member, said first thickness being dimensioned to effectively seal tissues disposed between the opposing jaw members upon electrosurgical activation and said second thickness being dimensioned to effectively cut tissue dispersed between the opposing jaw members upon electrosurgical activation.

* * * * *